United States Patent [19]

Smith

[11] Patent Number: 5,174,961
[45] Date of Patent: Dec. 29, 1992

[54] HIGH SENSITIVITY COAGULATION DETECTION APPARATUS

[75] Inventor: Leland B. Smith, Englewood, Colo.

[73] Assignee: HemoTec, Inc., Englewood, Colo.

[21] Appl. No.: 644,007

[22] Filed: Jan. 18, 1991

[51] Int. Cl.⁵ ............... G01N 31/02; G01N 33/50; G01N 35/00

[52] U.S. Cl. ........................... 422/73; 422/63; 422/68.1

[58] Field of Search ............ 422/63, 64, 73, 68.1, 422/67

[56] References Cited

U.S. PATENT DOCUMENTS

| | | |
|---|---|---|
| 2,129,043 | 9/1938 | Bortsch . |
| 3,077,106 | 2/1963 | Fink . |
| 3,302,452 | 2/1967 | Leslie . |
| 3,307,392 | 3/1967 | Owen et al. . |
| 3,450,501 | 6/1969 | Oberhardt . |
| 3,492,096 | 1/1970 | Hattersley . |
| 3,525,254 | 8/1970 | Milanes . |
| 3,560,162 | 2/1971 | Mittleman . |
| 3,560,163 | 2/1971 | Mittleman . |
| 3,587,295 | 6/1971 | Simons . |
| 3,635,678 | 1/1972 | Seitz . |
| 3,650,698 | 3/1972 | Adler . |
| 3,658,480 | 4/1972 | Kane et al. . |
| 3,692,487 | 9/1972 | Sanz . |
| 3,695,842 | 10/1972 | Mintz . |
| 3,699,437 | 10/1972 | Ur . |
| 3,704,099 | 11/1972 | Sanz . |
| 3,713,780 | 1/1973 | Shapiro . |
| 3,715,189 | 2/1973 | Nighohossian et al. . |
| 3,719,075 | 3/1973 | Mandrona et al. . |
| 3,741,002 | 6/1973 | Simons . |
| 3,814,585 | 6/1974 | Bailly . |
| 3,836,333 | 9/1974 | Mintz . |
| 3,854,324 | 12/1974 | Altshuler et al. . |
| 3,911,728 | 10/1975 | Fixot . |
| 3,918,908 | 11/1975 | Moyer et al. . |
| 3,963,349 | 6/1976 | Albright et al. . |
| 4,000,972 | 1/1977 | Braun et al. . |
| 4,026,671 | 5/1977 | Simons et al. . |
| 4,040,788 | 8/1977 | Simons et al. . |
| 4,058,367 | 11/1977 | Gilford . |
| 4,074,971 | 2/1978 | Braun et al. . |
| 4,081,242 | 3/1978 | Girolami . |
| 4,197,735 | 4/1980 | Munzer et al. . |
| 4,210,623 | 7/1980 | Breno et al. . |
| 4,285,906 | 8/1981 | Meltzer et al. ............ 422/61 |
| 4,362,698 | 12/1982 | Boosalis et al. . |
| 4,371,498 | 2/1983 | Scordato et al. . |
| 4,390,499 | 6/1983 | Curtis et al. . |
| 4,391,780 | 7/1983 | Boris . |
| 4,443,408 | 4/1984 | Mintz ..................... 422/73 |
| 4,533,519 | 8/1985 | Baugh et al. ............ 422/73 |
| 4,534,939 | 8/1985 | Smith et al. . |
| 4,551,308 | 11/1985 | Mintz ..................... 422/58 |
| 4,599,219 | 7/1986 | Cooper et al. ............ 422/61 |
| 4,612,801 | 9/1986 | Girolami . |
| 4,623,328 | 11/1986 | Hartranft ................. 604/4 |
| 4,663,127 | 5/1987 | Jackson et al. ........... 422/58 |
| 4,671,939 | 6/1987 | Mintz ..................... 422/58 |
| 4,752,449 | 6/1988 | Jackson et al. ........... 422/73 |
| 4,797,369 | 1/1989 | Mintz . |

Primary Examiner—Jill A. Johnston
Attorney, Agent, or Firm—John R. Ley; Bruce R. Winsor

[57] ABSTRACT

Coagulation related activities are detected in a fluid sample in a plunger sensor cartridge. The cartridge includes a test cell with a reagent chamber and a reaction chamber and a plunger assembly. A reagent drive subassembly forces the contents of the reagent chamber into the reaction chamber. The plunger assembly is raised and released by a plunger lifting subassembly to allow it to descend through the sample of liquid in the bottom of the reaction chamber. A dispenser subassembly automatically meters precise quantities of fluid into the test cells. The plunger lifting subassembly and the reagent drive subassembly are mechanically separate and are controlled separately. Stepper motors are used to provide precise control over the degree, rate and sensitivity of movement of the plunger lifting subassembly, the reagent drive subassembly and the dispensing subassembly.

27 Claims, 9 Drawing Sheets

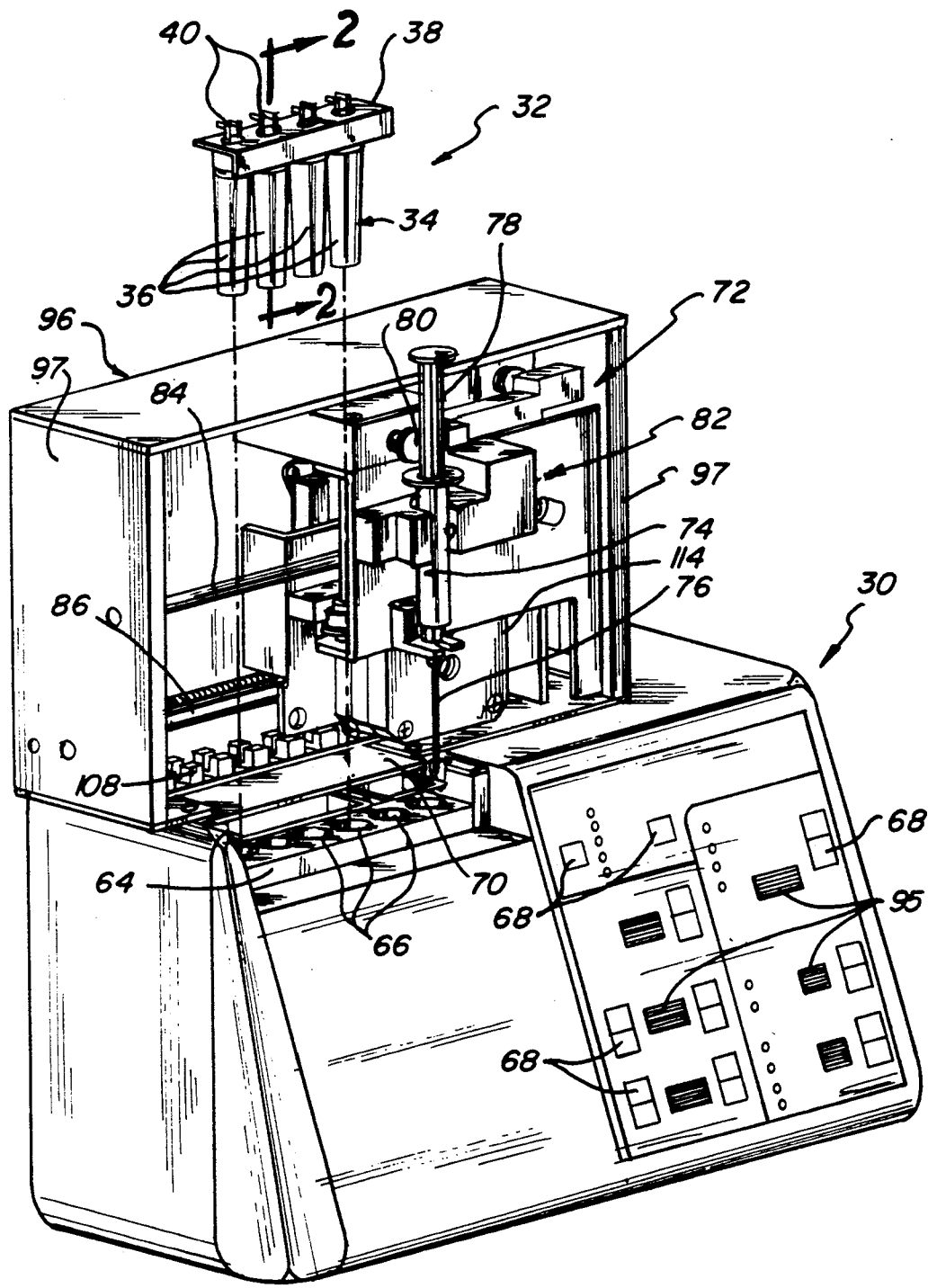
Fig_1

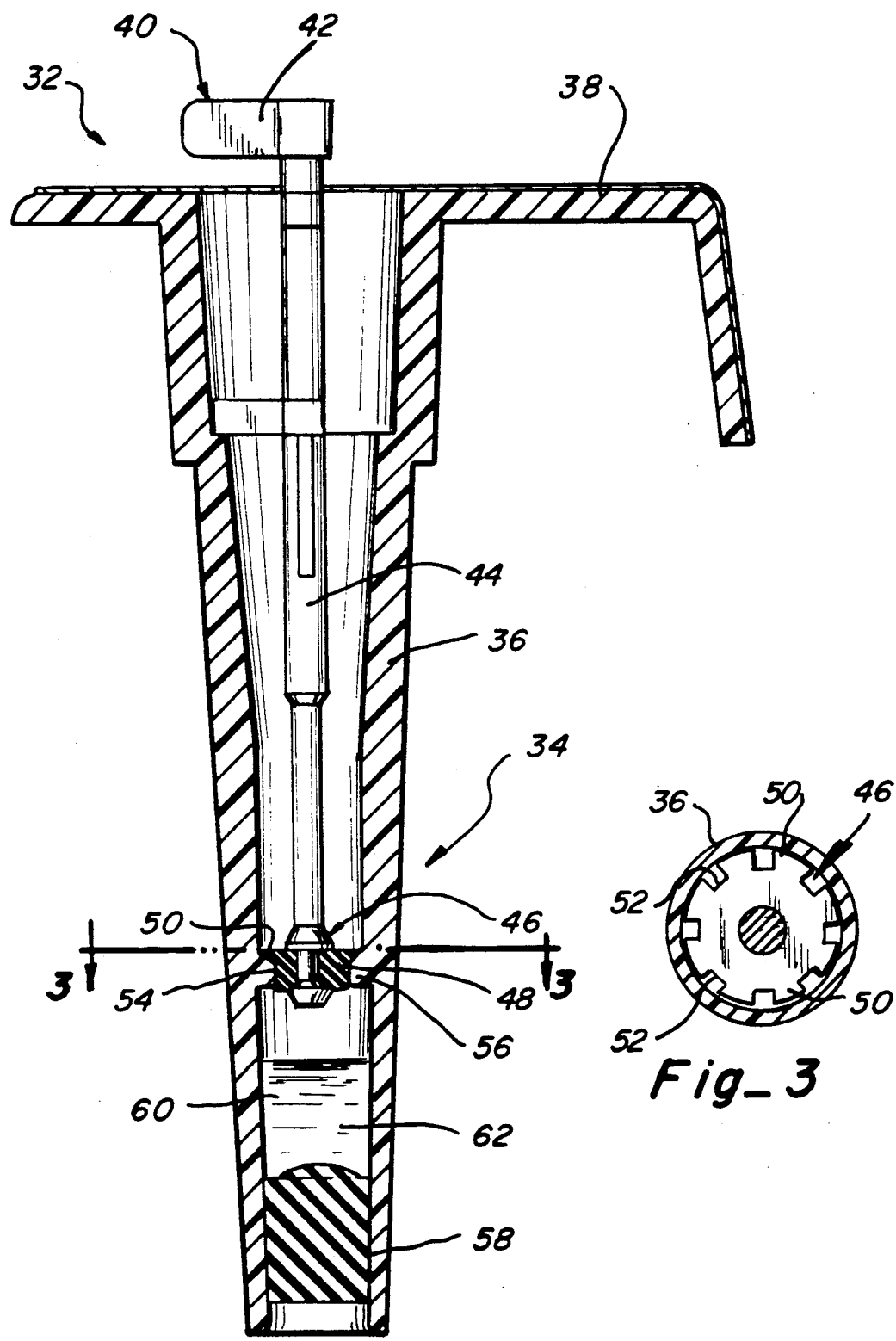
Fig_2
Fig_3

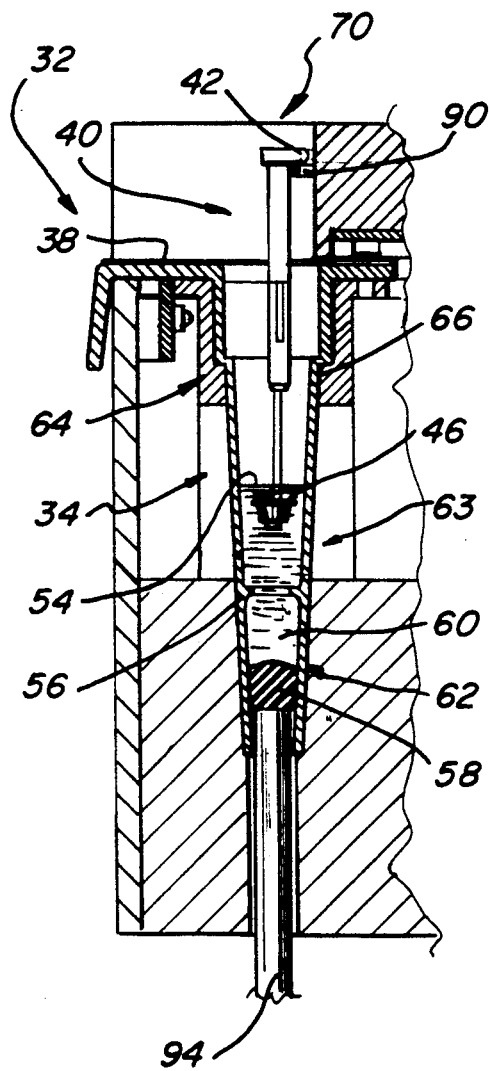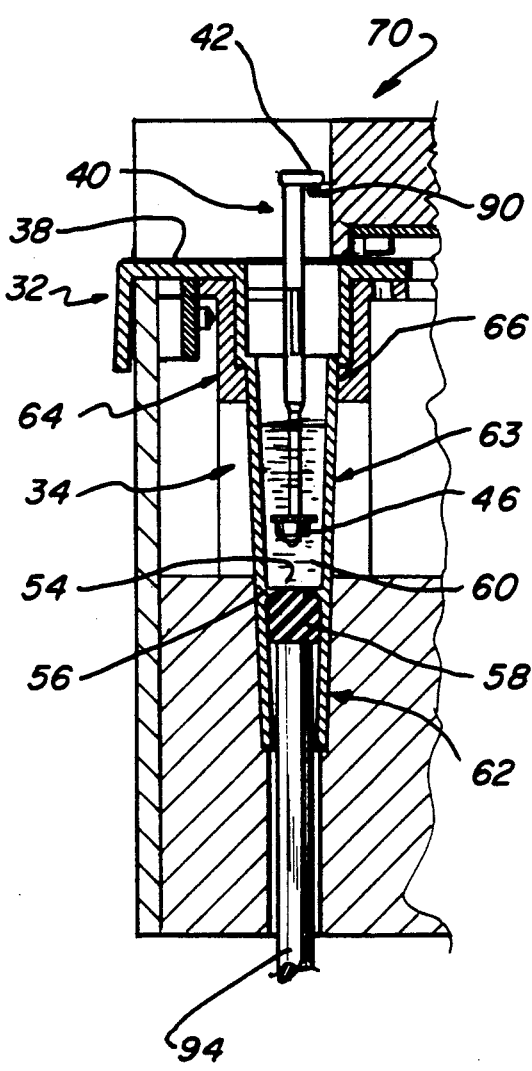
Fig_4A  Fig_4B

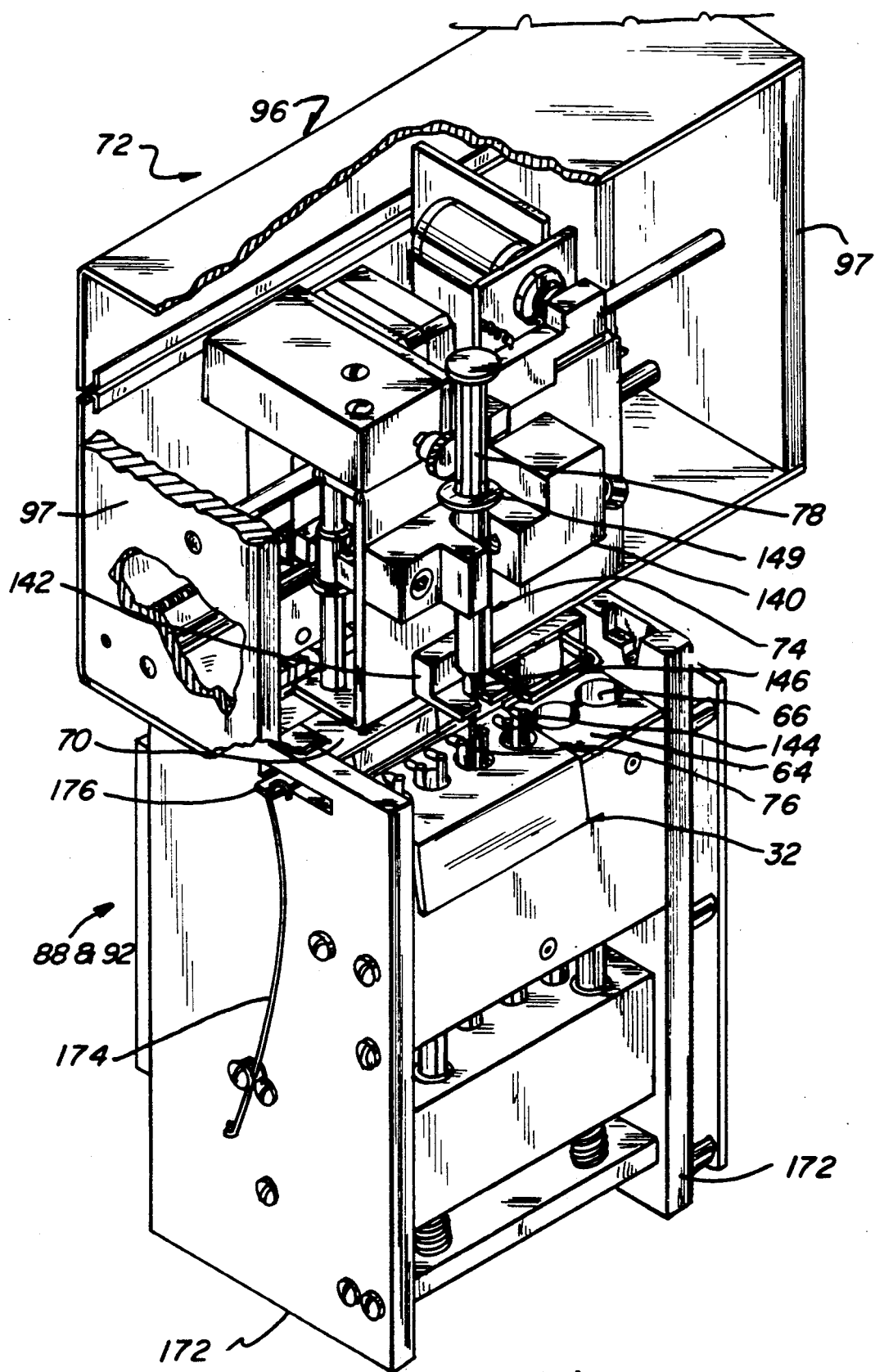
Fig_5

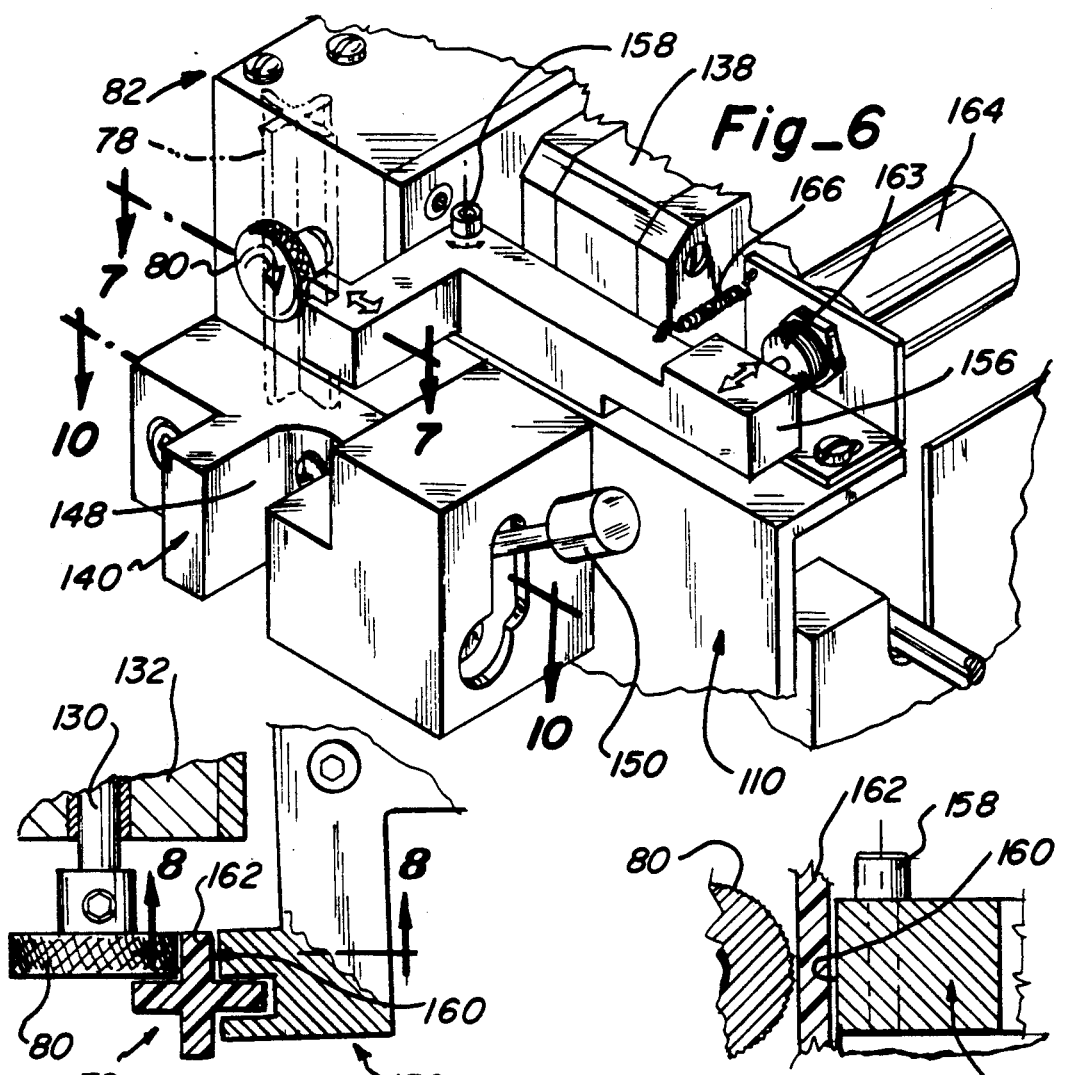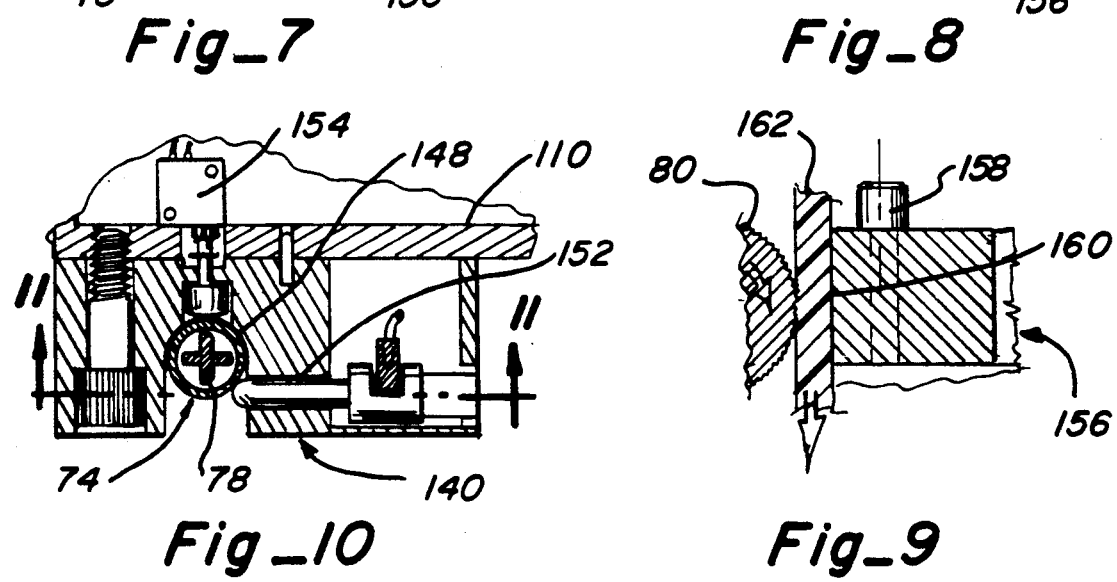

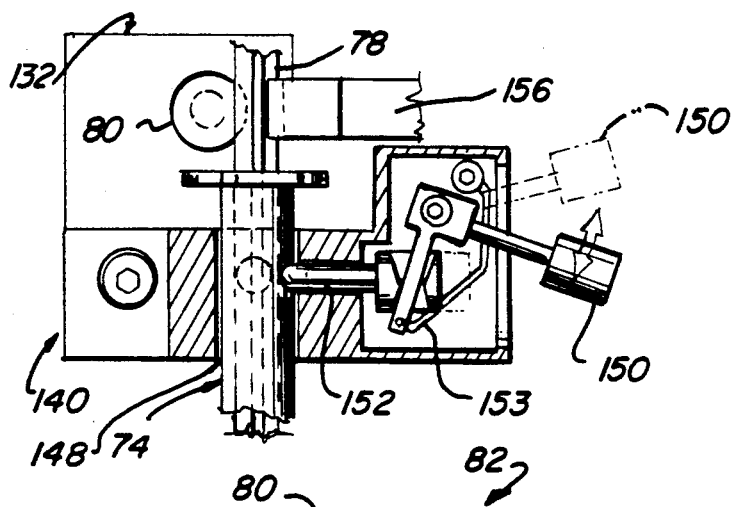
Fig_11
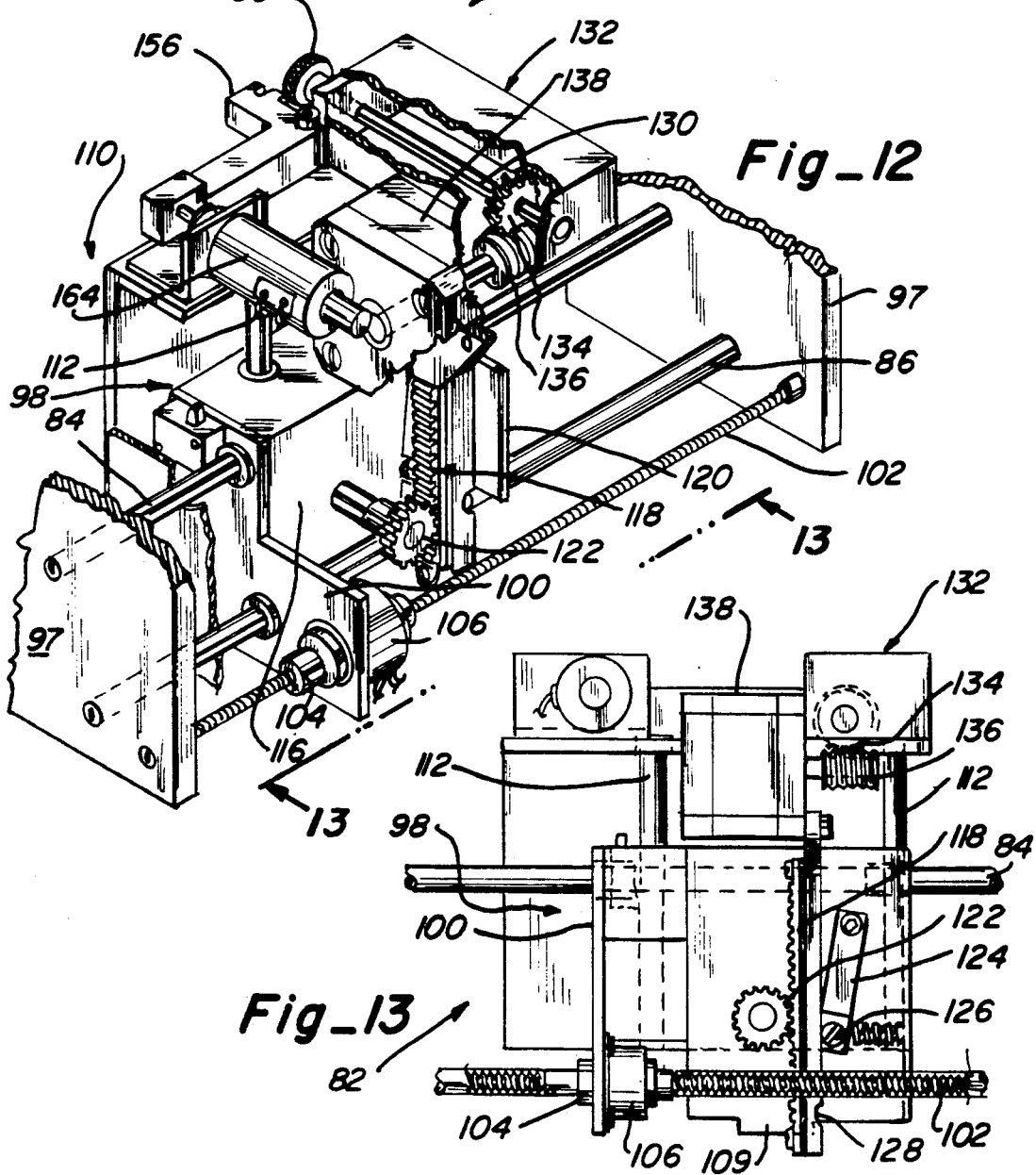
Fig_12
Fig_13

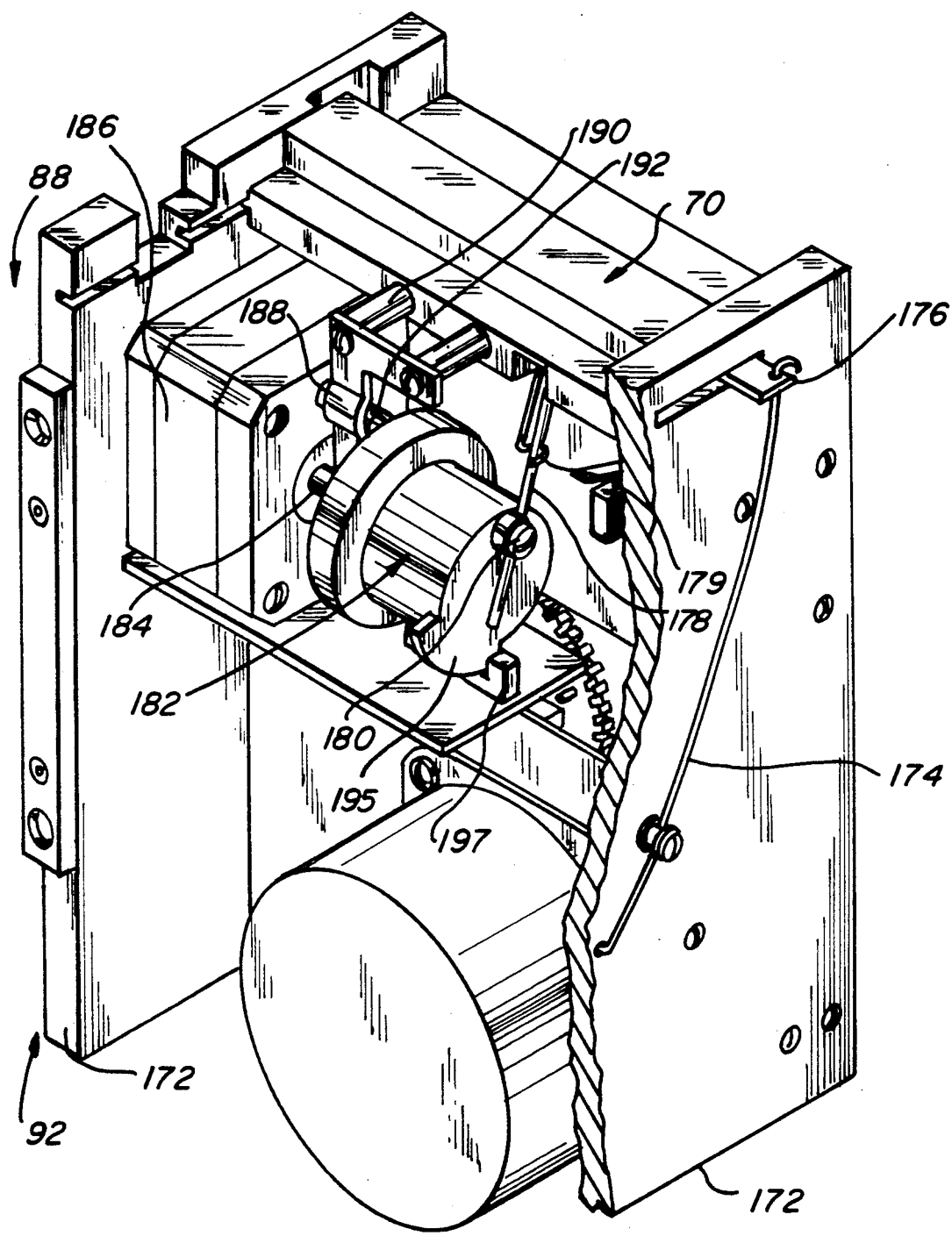
Fig_14

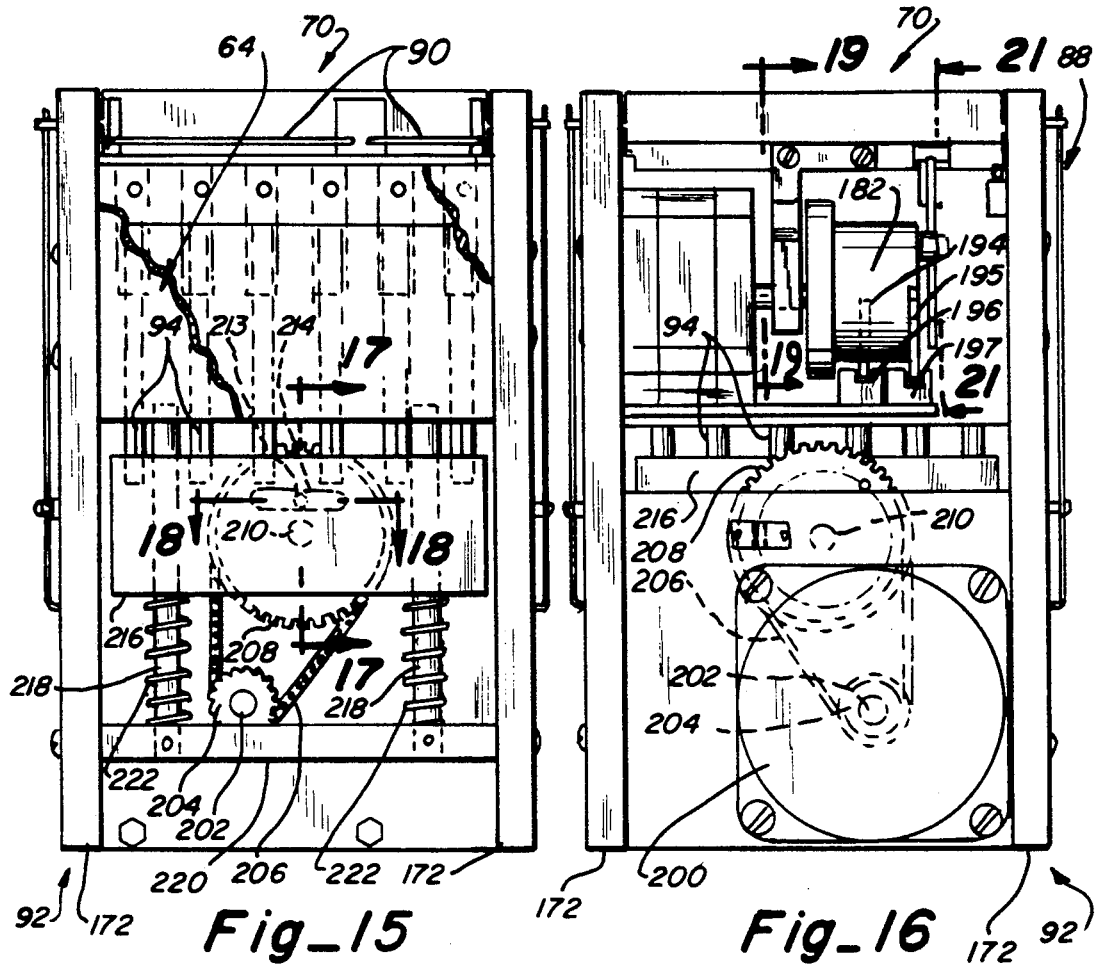
Fig_15  Fig_16
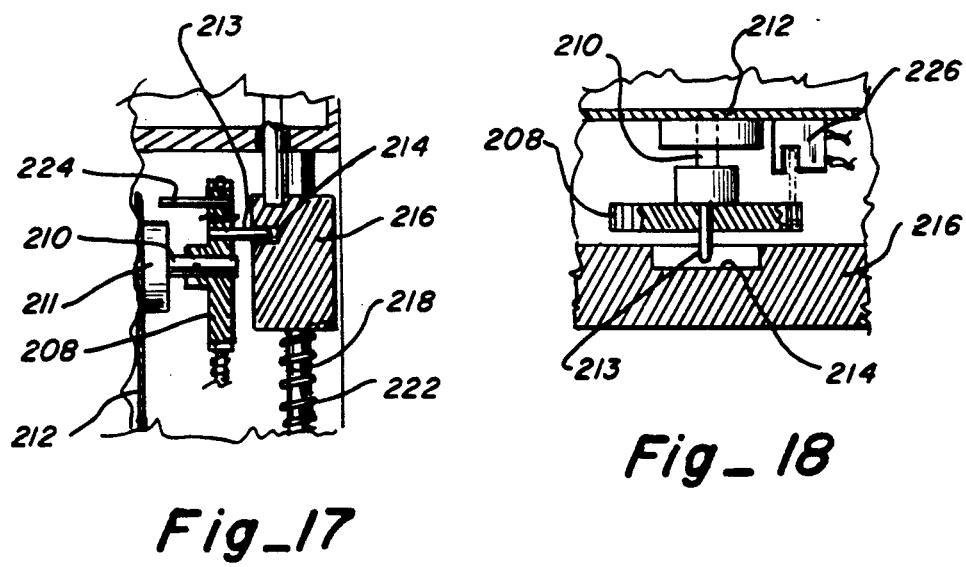
Fig_17  Fig_18

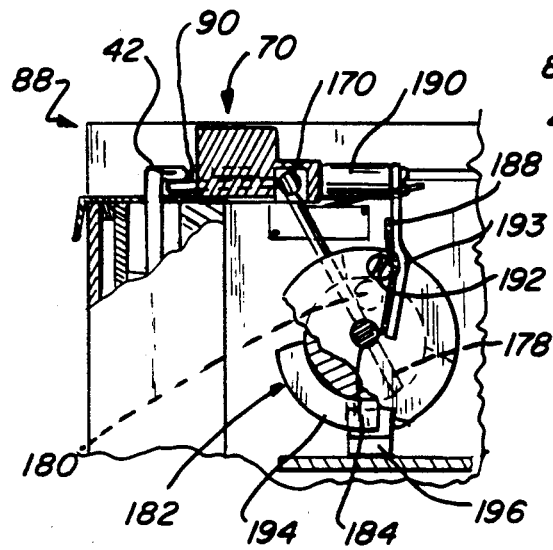
Fig_19
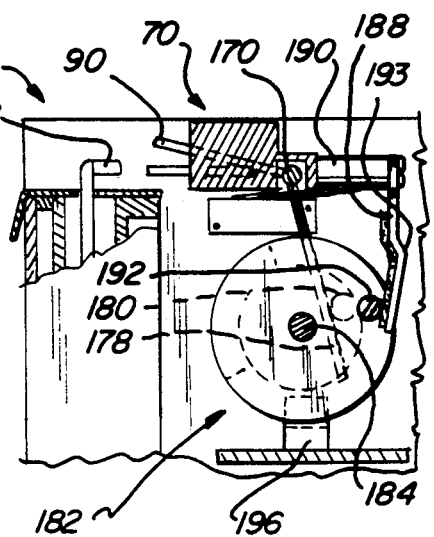
Fig_20
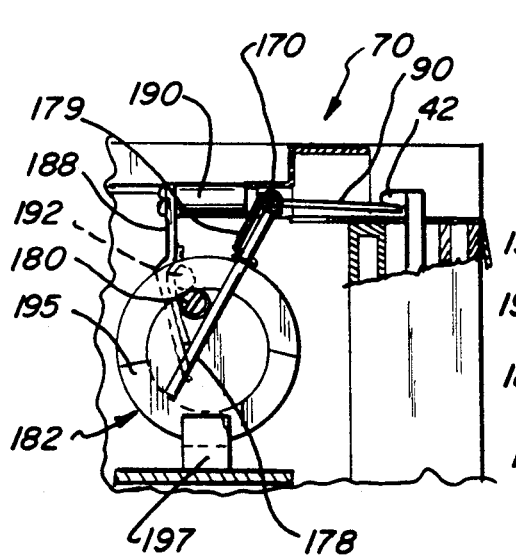
Fig_21
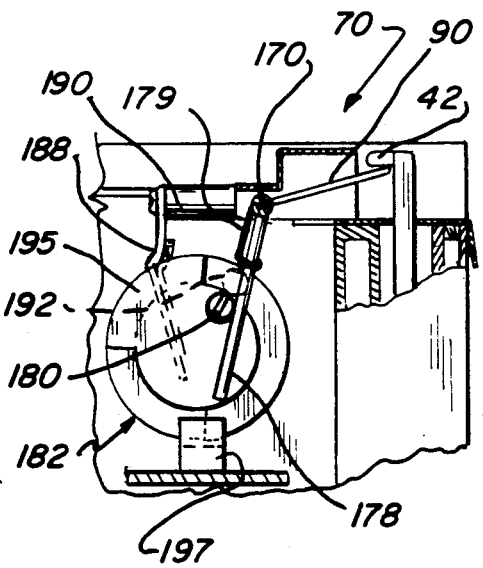
Fig_22

HIGH SENSITIVITY COAGULATION DETECTION APPARATUS

BACKGROUND OF THE INVENTION

This invention relates to measuring and detecting coagulation and coagulation related activities in fluids, particularly human blood. More particularly, the present invention relates to improvements in apparatus used for measuring and detecting coagulation and coagulation related activities in human blood by different types of coagulation analytical tests, particularly those involving a plunger sensing technique.

There exist a number of different apparatus and methods for measuring and determining coagulation and coagulation related activities of blood. Examples of previous apparatus and methods which employ a gas flow sensing technique for performing certain types of coagulation related analytical tests are U.S. Pat. Nos. 4,752,449 to Jackson et al.; 4,663,127 to Jackson et al.; 4,599,219 to Cooper et al.; 4,534,939 to Smith et al.; 4,533,519 to Baugh et al.; 4,074,971 to Braun et al.; and 4,000,972 to Braun et al., all of which are assigned to the assignee of the present invention. Examples of previous apparatus and methods which employ a plunger sensing technique for performing certain types of coagulation related analytical tests are U.S. Pat. Nos. 4,599,219 to Cooper et al.; and 4,752,449 to Jackson et al., both of which are assigned to the assignee of the present invention.

Many previous techniques for accomplishing some or all of the coagulation and the coagulation related analytical tests are subject to variable results and inaccuracies because human variations in test procedures are introduced by the technicians conducting the tests and because some of the procedures for the tests. For example, measuring the amounts of blood samples to be tested must be accomplished manually, despite the use of automated equipment to perform the tests. Some manual analytical tests require relatively long periods of time to complete. In many clinical situations, it is desireable to conduct the coagulation related tests on a "STAT" (immediate) basis. It is, therefore, recognized as desireable to provide automated apparatus which can reliably and consistently execute analytical tests under consistent, reproducible and relatively rapid conditions.

Automated apparatus employing the plunger technique of measuring and detecting coagulation and coagulation related activities generally comprise a plunger sensor cartridge or cartridges and a microprocessor controlled apparatus into which the cartridges are installed and which acts upon the cartridge to induce and detect the coagulation related event. The cartridge includes a plurality of test cells, each of which is defined by a tube-like member having an upper reaction chamber where a plunger assembly is located and where the analytical test is carried out and a lower reagent chamber which contains a reagent or reagents. A plug member seals the bottom of a lower reagent chamber. The contents of the lower reagent chamber are forced into the reaction chamber to be mixed with the sample of fluid usually human blood or its components when the test commences. An actuator, which is a part of the apparatus, lifts the plunger assembly and lowers it, thereby reciprocating the plunger assembly through the pool of fluid in the reaction chamber. The plunger assembly descends by the force of gravity, resisted only by a property of the fluid in the reaction chamber. When a property of the sample changes in a predetermined manner, the descent rate of the plunger assembly therethrough is changed. Upon a sufficient change in the descent, the coagulation related activity is detected and indicated by the apparatus.

Although previous apparatus using the plunger sensing technique have proven generally satisfactory, the need for certain enhancements has been identified. The mechanical construction and elements used in prior apparatus have tended to create a level of ambient noise and mechanical vibrations and movement, which is undesirable in a clinical setting, and which may actually interfere with precise and sensitive detection of subtle but significant aspects of coagulation related activity. In prior apparatus such as that described in U.S. Pat. No. 4,599,219 a reagent drive subassembly forced upward the plug at the bottom of the reagent chamber to collapse the reagent chamber contents into the reaction chamber. This reagent drive subassembly was mechanically coupled to move in unison with a plunger lifting subassembly which lifts and lowers the plunger assembly. Since a relatively large amount of force is required to simultaneously force upward the plugs of a plurality of test cells in a cartridge, a relatively large motor is required. The relatively large motor limited the ability to obtain precise control over the rates and extent of movement of the plunger lifting assembly, particularly because of the relatively large amount of mechanical inertia associated with repeatedly reciprocating the elements of the reagent drive subassembly simultaneously with reciprocating the plunger lifting subassembly. Furthermore, it has been determined that many coagulation related tests may require independent control over the movement of the plug to collapse the reagent chamber contents into the reaction chamber and the movement of the plunger assembly at the commencement of the analytical test. This feature was, of course, impossible to achieve with the prior apparatus which mechanically linked the plunger lifting subassembly to the reagent drive subassembly for simultaneous movement.

The prior apparatus also required manual insertion and measurement of the fluid samples into each test cell. Because of human induced variances in the quantity of the sample introduced into each test cell, reliable and accurate results were only possible with relatively large blood samples of approximately 1.5 mL. Samples of a relatively large size were required because smaller samples could not be accurately measured by the technician, except with a pipetter. Experience has shown that in clinical settings, and particularly under STAT conditions, technicians will frequently choose to meter the sample into the cartridges by less accurate methods, such as with a syringe, thereby accepting inaccurate or incompetent test results, rather than utilize the time consuming method of pipetting the blood. The use of the larger sample size also reduced the variance in test results introduced because of the variance in the sample size, because the degree of sample size variance could be reduced relative to the size of the sample. Larger sample sizes also require larger cartridges for some tests and greater quantities of reagent, thereby increasing the cost of the cartridges. Sometimes, the larger sample size made the finer and more subtle coagulation related changes more difficult or impossible to detect. The need to use large sample sizes requires larger quantities of blood to be collected from the patient, and/or reduces the quantity of blood which might be available for other medical tests.

It has been determined, therefore, as advantageous to improve the prior art coagulation detection apparatus to overcome these and other difficulties and undesirable effects. It is against this background that significant improvements and advancements have evolved.

SUMMARY OF THE INVENTION

One of the significant aspects of the present invention is separation of the functions of the plunger lifting subassembly from those of the reagent drive subassembly. By separating these functions and providing a separate drive motor for each subassembly, the drive motor for the plunger lifting subassembly can be reduced in size and made more controllable and sensitive. The mass of mechanical elements that the reagent drive subassembly motor must move with each cycle is reduced. This reduction in mass has the added advantage of reducing the noise to a more satisfactory level. Separation of the motors and functions also permits each function movement to be controlled to operate in the manner, and with relative timing, best suited for the particular analytical test. In accordance with this aspect of the present invention, the coagulation detection apparatus of the present invention employs a plunger lifting subassembly and a reagent drive subassembly which are mechanically separated to be operated with separate drive motors and mechanical components.

Another significant aspect of the present invention is the use of an automated dispensing system for precisely metering the fluid sample to be tested into the test cells of the cartridges. More precise control of the quantities of the fluid samples inserted into the test cells is obtained. The present invention permits the operator to manually attach a fluid-filled conventional medical syringe onto the dispensing subassembly, and the dispensing subassembly then automatically positions the syringe over each of the test cells and dispenses a precisely controlled amount of fluid into each cartridge. The dispensing subassembly is programmable to vary the quantity of the fluid sample metered into each test cell, and to allow different quantities to be metered into different test cells and different cartridges, in accordance with the analytical test being conducted. In accordance with this aspect the coagulation detection apparatus of the present invention incorporates a dispensing subassembly which achieves these desirable aspects of functionality.

Still another significant aspect of the present invention is the use of the plunger lifting subassembly, the reagent drive subassembly and the dispensing subassembly in a single coagulation detection apparatus. The combination of these three subassemblies in a single apparatus achieves improvements in the ability of a coagulation detection apparatus to detect coagulation related activity. By using separate stepper motors to control the functionality of these subassemblies, it is possible to obtain more precise control over the speed, movement, frequency and stroke length of each of the operations associated with each subassembly, further enhancing operational flexibility and sensitivity. Furthermore the number and type of analytical tests which can be accurately performed is greatly enhanced.

A more complete appreciation of the present invention and its scope can be obtained from understanding the accompanying drawings, which are briefly summarized below, the following detailed description of a presently preferred embodiment of the invention, and the appended claims.

BRIEF DESCRIPTION OF THE DRAWINGS

FIG. 1 is a perspective view of a new high sensitivity coagulation detection apparatus embodying the present invention and a plunger sensor detection cartridge used in conjunction with the apparatus, including an improved plunger lifting subassembly, an improved reagent driver subassembly, and a sample dispensing subassembly, all of which operate in conjunction with the cartridge.

FIG. 2 is a vertical sectional view of a test cell of the cartridge shown in FIG. 1, taken substantially in the plane of line 2—2.

FIG. 3 is a horizontal sectional view taken substantially in the plane of line 3—3 in FIG. 2.

FIGS. 4A and 4B are sectional views similar to those shown in FIG. 2, illustrating the elements of the apparatus and the test cell of the cartridge at the commencement of and during the course of a coagulation related test.

FIG. 5 is a front perspective view of the plunger lifting subassembly, the reagent drive subassembly, and the sample dispensing subassembly, of the apparatus shown in FIG. 1.

FIG. 6 is an enlarged partial front perspective view of a portion of the dispensing subassembly shown in FIG. 5.

FIG. 7 is a horizontal sectional view taken substantially in the plane of line 7—7 in FIG. 6.

FIG. 8 is a vertical sectional view of a portion of the apparatus shown in FIG. 7, taken substantially in the plane of line 8—8 in FIG. 7.

FIG. 9 is a view similar to that shown in FIG. 8.

FIG. 10 is a horizontal sectional view taken substantially in the plane of line 10—10 in FIG. 6.

FIG. 11 is a vertical sectional view taken substantially in the plane of line 11—11 in FIG. 10.

FIG. 12 is a rear perspective view of a portion of the dispenser subassembly shown in FIG. 5.

FIG. 13 is rear vertical elevational view of a portion of the dispenser subassembly shown in FIG. 12.

FIG. 14 is a rear perspective view of the plunger lifting subassembly and the reagent drive subassembly shown in FIG. 5.

FIG. 15 is a front elevational view of the plunger lifting subassembly and the reagent drive subassembly shown in FIG. 14.

FIG. 16 is a rear elevational view of the plunger 10 lifting subassembly and the reagent drive subassembly shown in FIG. 15.

FIG. 17 is a vertical sectional view taken substantially in the plane of line 17—17 in FIG. 15.

FIG. 18 is a horizontal sectional view taken substantially in the plane of line 18—18 in FIG. 15.

FIG. 19 is a vertical sectional view taken substantially in the plane of line 19—19 in FIG. 16.

FIG. 20 is a vertical sectional view similar to that shown in FIG. 19, illustrating the elements in another position.

FIG. 21 is a vertical sectional view taken substantially in the plane of line 21—21 in FIG. 16.

FIG. 22 is a vertical sectional view similar to that shown in FIG. 19, illustrating the elements in another position.

DETAILED DESCRIPTION

A presently preferred embodiment of an apparatus 30 and a plunger sensor cartridge 32 which are used together in order to perform coagulation and coagulation related activity tests on samples of fluid such as blood or components of blood is illustrated in FIGS. 1 and 2. In general, many of the coagulation related tests which may be performed using the apparatus 30 and the cartridge 32 have previously been described in the assignee's aforementioned patents, including U.S. Pat. No. 4,599,219, the disclosure of which is incorporated herein by this reference. Accordingly, many of the details of functionality will be generalized herein with the understanding that the applicant's prior patents disclose many of these details in a greater extent.

In general, the cartridge 32, as shown in FIG. 2, includes a plurality of test cells 34, each of which is formed generally as a downward extending truncated tube-like member 36. Each of the tube-like members 36 is connected to an upper shelf portion 38. A plunger assembly 40 extends downward from an upper open end of each test cell 34 into the tube-like member 36. Each plunger assembly 40 includes a pair of flags 42 at the upper end located at a position above the shelf portion 38. The plunger assembly 40 also includes a shaft 44 which extends from the flags 42 downward to a lower end upon which a disk member 46 is attached. The disk member 46 is formed of resilient material and includes a center generally cylindrical main body portion 48 and an annular flange 50 located above and extending outward from the main body portion 48. As is shown in FIG. 3, the annular flange includes slots or openings 52 formed therein at outer circumferential locations.

As shown in FIG. 2, prior to using the plunger sensor cartridge 32 in the apparatus 30, the disk member 46 is positioned with its main body portion 48 located in and sealed against an opening 54 formed by a partition 56 extending inwardly from the tube-like member 36. The partition 56 is located between the upper and lower open ends of the tube-like member 36. A resilient flexible plug 58 is positioned in the interior of the tube-like member at its lower open end. The plug 58 seals against the inner side walls of the tube-like member 36 and confines a quantity of reagent 60 in a reagent chamber 62 between the partition 56 and the plug 58. The reagent 60 may be a liquid or a solid powder and is selected in accordance with the type of coagulation-related test which is performed. A reaction chamber 63 is generally defined by that portion of the open tube-like member 36 above the partition 56.

FIGS. 2, 4A and 4B illustrate the operation of the plunger sensor cartridge 32. At the commencement of an analytical coagulation related test, a sample of fluid upon which the test is to be performed is introduced into the reaction chamber 63. The plunger assembly 40 is lifted to withdraw the disk member 46 from its seated engagement with the opening 54 in the partition 56. See FIG. 4A. The plug 58 is pushed upward against the partition 56 and the reagent 60 from the reagent chamber 62 is forced through the opening 54 into the reaction chamber 63. See FIG. 4B. The reagent 60 is mixed with the fluid sample in the reaction chamber, preferably by a short period of reciprocating of the plunger assembly 40. The plunger lifting subassembly of the present invention controls the lifting movement of the plunger assembly 40, and the reagent drive subassembly of the present invention moves the plug 58 to force the reagent 60 into the reaction chamber 63. An optical sensing system (not shown) senses the physical descent of the plunger assembly through the sample and reagent in order to detect the coagulation-related condition.

As may be understood by reference to FIGS. 1, 4A, 4B, and 5, the plunger sensor cartridge 32 is inserted into a receiving block 64 in the apparatus 30 to conduct a coagulation related test. Each of the test cells 34 extend into a receptacle 66 of the receiving block 64. See FIGS. 4A and 4B. Each receptacle 66 has a configuration adapted to receive a test cell 34, while the shelf portion 38 of the cartridge 32 sits on top of the block 64.

A coagulation related test is commenced by the operator depressing on of the control switches 68 (FIG. 1) located on the exterior housing of the apparatus 30. The apparatus 30 is preferably controlled by a microprocessor which causes operation of the components pertinent to the present invention to occur in the manner described below.

Upon the commencement of a test, a cartridge retaining member 70 moves forward and contacts an edge of the shelf portion 38 to hold the cartridge 32 with the test cells 34 in the receptacles 66. The retaining member 70 includes a plurality of optical sensors (not shown) adapted to sense indications on the rearward facing (as shown in FIG. 1) edge of the shelf portion 38. In this manner, information regarding the cartridge 32, the type of analytical test to be performed and the location of the test cells of the cartridge in the receiving block 64 is optically determined. Thus, cartridges having a number of test cells less than the full number of receptacles 66 may be inserted in the receiving block 64 and used with the apparatus 30.

After sensing the information associated with the cartridge, the retaining member 70 withdraws to a partially retracted position, and a sample dispensing subassembly 72 (FIG. 1) injects a predetermined precise amount of fluid sample into each test cell 34 of the plunger sensor cartridge 32 retained in the receiving block 64.

Details of the sample dispensing subassembly 72 are shown in FIGS. 5 to 13. The sample of fluid is obtained from a conventional syringe 74 having a blunt needle 76 attached thereto. The syringe 74 is manually attached to the dispensing subassembly 72. The body of the syringe 74 contains a sample of fluid, such as blood, upon which the coagulation related test is to be performed. To perform STAT tests, the same syringe body which was used to collect the blood for the sample, may be connected to the dispensing subassembly 72, after attaching the blunt needle 76. Of course, prior to attachment of the syringe 74 to the dispensing subassembly 74, all air or other voids in the fluid within the syringe 74 and the blunt needle 76 is removed in the conventional manner. A plunger 78 located within the body of the syringe 74 is engaged with a drive wheel 80. See FIG. 7 to 9. Rotation of the drive wheel 80 forces the syringe plunger 78 downward and expels a predetermined amount of fluid from the lower end of the blunt needle 76 (FIG. 5). Of course, the extent to which the syringe plunger 78 is moved downward determines the quantity of fluid expelled from the needle.

The dispensing subassembly 72 includes a movement frame 82 (FIG. 12) which is moved laterally in the horizontal direction along guide rods 84 and 86. The degree of lateral movement is controlled by the microprocessor (not shown) of the apparatus 30 (FIG. 1) in accordance with the information of the signals obtained from the optical sensors in the retaining member 70 and other programmed information, thereby locating the blunt needle 76 directly above the open upward ends of each test cell 34 of the cartridge 32. After attaining the proper lateral location, the movement frame 82 moves the syringe 74 vertically downward to insert the lower end of the blunt needle 76 into each of the test cells. The desired amount of fluid sample is automatically dispensed into the test cell. Thereafter, the blunt needle 76 is withdrawn from the test cell 34 by the movement frame 82, and the next lateral position over a test cell is assumed. The sequence again repeats itself, thereby injecting into each test cell of the plunger sensor cartridge that predetermined amount of fluid sample needed for conducting the particular test. The quantity of sample injected in each of the test cells may be the same in all of the test cells or may vary in accordance with the particular type of test to be performed. With the fluid samples dispensed into each of the test cells 34 of the plunger sensor cartridge 32, the movement frame 82 moves laterally (to the right as shown in FIG. 1) to avoid contact with the other subassemblies.

A plunger lifting subassembly 88 is shown in FIGS. 5, 14 to 16, and 19 to 22, and includes at least one and preferably a plurality of lift wires 90. The lift wires 90 are carried by and moved forward with the retaining member 70 (FIG. 19). Preferably a plurality of lift wires 90 (FIG. 15) are employed to accommodate cartridges 32 of different sizes, that is, those cartridges having different numbers of test cells. For example, cartridges having two, four and six test cells can be accommodated by the right and left lift wires 90 as shown in FIG. 15. The lift wires 90 are positioned in a lowermost location when the retaining member 70 reaches its forward position, and in that position a horizontal segment of the lift wires fit underneath the flags 42 (FIG. 19) of the plunger assembly shaft 44 (FIG. 2). Upward movement of the lift wires 90 lifts each of the plunger assemblies 40 upward, thereby removing the disk member 46 from its sealed location in the opening 54 of the partition 56 as is shown in FIG. 4A. A fluid communication passageway through the opening 54 between the reagent chamber 62 and the reaction chamber 63 is thereby established. A reagent drive subassembly 92, shown in FIGS. 5 and 14 to 18, includes a plurality of plug driver shafts 94. Thereafter, or simultaneously with the upward movement of the plunger assembly 40, one of a plurality of plug driver shafts 94 of the reagent drive subassembly 92 moves upward, forcing each plug 58 upward, collapsing the reagent chamber 62 and forcing its contents 60 into the reaction chamber 63. This condition is illustrated in FIG. 4B By first lifting the plunger assembly 40 before collapsing the reagent chamber 62 (FIG. 4A), the communication passageway through the opening 54 is opened to allow the fluid sample to mix with the reagent 60 before the reagent chamber 62 is collapsed. This avoids trapping bubbles in the reagent chamber when it collapses.

Thereafter, the lift wire 90 repeatedly lifts and lowers the plunger assembly 40 and causes agitation to mix the fluid sample and the reagent within the reaction chamber 63 at the beginning of the test. The degree and amount of mixing depends on a number of factors 15 particular to the type of coagulation related test. After mixing is complete, the lifting and lowering of the plunger assembly 40 continues, but possibly at a different rate. As a property of the sample mixed with the reagent changes, the descent of the plunger assembly 40 relative to the lowering movement of the lift wire 90 changes. Since the tube-like member 36 of each test cell 34 is formed of clear material such as plastic, optical sensors (not shown), which are located within the interior of each receptacle 66 of the receiving block 64, are used for the purpose of monitoring the descent of the plunger assembly 40 relative to the descent of the lift wire 90. Once a change of a predetermined magnitude is detected, the coagulation related activity of the sample is determined to have occurred. The time for this activity to have occurred, or other information related to the activity, may be displayed on displays 95 (FIG. 1) present on the outside housing of the apparatus 30.

Details regarding the improved nature of the dispensing subassembly 72, the plunger lifting subassembly 88, and the reagent drive subassembly 92 are set forth in greater detail below.

Details regarding the dispensing subassembly 72 are illustrated in FIGS. 5 to 13. The dispensing subassembly 72 includes a frame housing 96 having side walls 97 between which the guide rods 84 and 86 (FIG. 12) extend. As shown in FIG. 12 the movement frame 82 includes a main block member 98 through which the upper guide rod 84 extends. A side plate 100 is connected to the main block member 98. The side plate includes a bushing through which the lower guide rod 86 extends. All of the other elements of the movement frame 82 are connected to the main block member 98 and the side plate 100.

A threaded rod 102 also extends between the side walls 97 of the frame housing 96, and the rods 84, 86 and 102 are all oriented parallel to one another in a horizontal direction. The movement frame 82 is supported for lateral movement on the rods 84 and 86, and is moved laterally therealong as a result of the rotation of an armature 104 of a lateral movement stepper motor 106. The armature 104 is threaded onto the threaded rod 102. As a result, the operation of the lateral movement stepper motor 106 laterally moves the movement frame 82.

The lateral movement stepper motor 106, as well as the other stepper motors employed throughout the present invention, are preferably utilized in order to be directly controlled by driving pulses generated by microprocessor control. In addition, the number of driving pulses is directly related in a highly precise manner to the amount of rotation achieved by the motor. This rotational movement is translated into linear movement in each of the cases described below, thereby achieving a high degree of precision over the extent of linear movement of each of the affected devices.

The extent of precise lateral movement obtained by rotation of the stepper motor 106 to position the movement frame 82 above each open test cell is controlled by optical sensors 108 (FIG. 1) which are attached to the frame housing 96 at the predetermined locations necessary to position the syringe needle 76 above each open test cell. A light path from the optical sensors 108 is broken by a shutter or vane 109 (FIG. 13) attached to the movement frame 82. As a result, signals are derived to limit the rotation of the stepper motor 106 for positioning the movement frame 82, under control of the microprocessor.

A front support plate 110 is moveably connected by a pair of vertical guide rods 112 to the main block member 98. Bushings between the vertical guide rods 112 and the main block member 98 allow the support plate 110 to move vertically with respect to the main block member 98 and with respect to the guide rods 84 and 86. Vertical movement of the movement frame 82 is controlled by a vertical movement stepper motor 114 (FIG. 1), which is attached to a mounting bracket 116 that is connected to the main block member 98. See FIGS. 12 and 13. A tooth track member 118 is vertically oriented and connected to a bracket 120 on the front support plate 110. The vertical track member 118 may comprise a ladder belt attached to a mounting block or a toothed rack. A pinion gear 122 is attached to the drive shaft of the vertical stepper motor 114, and the teeth of the gear 122 mesh with the teeth of the vertical rack member 118. Rotation of the gear 122 by the stepper motor 114 translates into linear movement of the vertical track member 118, and the support plate 110. Accordingly, the syringe 74 is thereby moved vertically downward along with the front support plate 110 to position the blunt needle 76 (FIG. 5) into each test cell 34.

A spring biased detent 124 (FIG. 13) includes a projection 126 which fits within a notch 128 of the tooth track member 118. The spring force applied through the projection into the notch 128 is sufficient to hold the elements of the movement frame in the upward position under most conditions of non-use. However, the linear force available from the stepper motor 114 is sufficient to overcome the spring force of the detente in order to move downward the movement frame and the support plate 110.

A syringe drive shaft 130 (FIG. 12), which is connected to the drive wheel 80, is positioned within a shaft housing 132 that is attached to the top of the support plate 110. The rear end of the drive shaft has attached thereon a worm gear 134 which meshes with a worm screw 136 attached to a syringe drive stepper motor 138. The syringe drive stepper motor is also attached to the shaft housing 132. Rotation of the stepper motor 138 is thus translated into rotation of the drive wheel 80 which forces the syringe plunger 78 (FIGS. 6 to 9) downward into the body of the syringe 74 (FIG. 5) and expels a predetermined amount of fluid from the needle 76. The amount of fluid expelled is directly related to the linear movement of the syringe plunger 78, and that amount of movement is directly related to the degree and extent of rotation of the stepper motor 138, under the control of the microprocessor.

The body of the syringe 74 with the attached blunt needle 76 is supported from the support plate 110 by a retaining block 140 and a bracket 142. See FIG. 5. An opening 144 in the shape of a keyhole is formed in the bracket 142. A circular portion of the opening 144 receives a hub and flange 146 of the blunt needle 76. An elongated channel 148 with a circular back wall is formed in the retaining block 140 (FIGS. 6 and 10), to receive therein the cylindrical body of the syringe 74. The outward extending flange 149 (FIG. 5) on the top of the syringe body is positioned above the surface of the retaining block 140. Force is transmitted from a lever 150 (FIG. 6) to a retaining pin 152 (FIGS. 10 and 11) which projects into the channel 148 in order to frictionally engage the body of the syringe 74 and hold it in place. The mechanism for transferring the movement to the pin 152 is conventional, and includes an over center spring 153 (FIG. 11) in order to hold the pin 152 into engagement with the syringe body, or to hold the pin 152 in a retracted position not projecting into the channel 148. A button located in the curved rear wall of the channel 148, is connected to an electrical switch 154 (FIG. 10). The button is depressed upon the insertion of the syringe body into the channel. Depression of the button activates the switch 154 and signals the microprocessor that the syringe 74 is in place in the dispensing subassembly 72.

An L-shaped syringe plunger engagement lever 156 (FIG. 6) is pivotally connected to the support plate 110 by an attachment screw 158. As shown in FIGS. 7 to 9, a smooth engagement surface 160 faces the drive wheel 80 and forces one rib 162 of the syringe plunger 78 into engagement with the drive wheel 80. The exterior circumferential surface of the drive wheel 80 is knurled, to provide sufficient frictional engagement with the rib of the syringe plunger 78 to propel the syringe plunger 78 downward into the syringe body 74 as the drive wheel 80 rotates. The engagement surface 160 is smooth to allow the side of the plunger rib to slide therealong without significant impediment. The other end of the engagement lever 156 is engaged by the armature 163 of a solenoid 164, which is attached by a mounting bracket 165 to the support plate 110. See FIG. 6. Upon energizing the solenoid 164, the armature 163 moves forward, thus pivoting the engagement lever 156 and forcing the engagement surface 160 against the plunger rib 162 and causing the knurled drive wheel 80 to engage the syringe plunger to obtain plunger movement upon rotation of the stepper motor 138. See FIGS. 8 and 7. Of course, energization of the solenoid 164 is controlled by the microprocessor, as well as the degree of rotation of the stepper motor. A biasing spring 166 (FIG. 6) returns the engagement lever 156 to its disengaged position upon deenergization of solenoid 164.

As described, the dispensing subassembly 72 automatically holds the syringe 74, moves laterally to position the blunt needle 76 of the syringe above each test cell, moves vertically to position the needle 76 near the bottom of the reaction chamber 63 in each test cell 34, to thereupon deliver a precise amount of sample from the syringe into the reaction chamber 63, and to repeat this sequence until all the test cells in a cartridge 32 have been filled.

The plunger lifting subassembly 88 is illustrated in FIGS. 14 to 16 and 19 to 22. The plunger lifting subassembly 88 includes the retaining member 70 and a pivot shaft 170 (FIG. 19–22) to which the lift wires 90 are connected. The retaining member 70 is positioned between two side frame plates 172 (FIG. 14) to which the elements of the plunger lifting subassembly 88 and the reagent drive subassembly 92 are connected. An elongated spring wire 174 contacts a tab 176 connected to the retaining member 70 and the frame plates 172. The spring wire 174 biases the retaining member 70 to the forward position. As shown in FIGS. 19 to 22, a pivot arm 178 is connected to the pivot shaft 170, is biased to hold the lift wire in a lowered position by a coil spring 179, and contacts a first cylindrical projection 180 attached to a vertical surface of a wheel 182. The wheel 182 is connected to a shaft 184 of a plunger lifting stepper motor 186 (FIG. 14). Rotation of the plunger lifting stepper motor 186 rotates the wheel 182 and the resulting arc-like movement of the projection 180 causes the lift wire 90 to be raised and lowered as a result of pivoting about the pivot shaft 170. An arm 188 is attached to an extension 190 of the retaining member 70. The arm 188 contacts a second cylindrical projection 192 attached to the side of the wheel 182 opposite the first projection 180. Rotation of the wheel 182 and the resulting arc-like movement of the projection 192 causes the retaining member 70 to move between the forward position shown in FIG. 19 and the rearward position shown in FIG. 20. Thus rotational movement of the wheel 182 both moves the retaining member 70 and reciprocates the lift wire 90, as will be described in greater detail below.

The forward and rearward movement of the retaining member 70 is controlled in the manner shown in FIGS. 19 and 20, respectively. When the wheel 182 is rotated to position the second cylindrical projection 192 at the rearward most position as shown in FIG. 20, the arm 188 moves the retaining member 70 rearwardly. Upon rotation of the wheel 18 to position the cylindrical projection 192 at a vertical top position shown in FIG. 19, which is approximately 90 degrees counterclockwise from that position shown in FIG. 19, the retaining member 70 moves forward from the force from the spring wires 174. Thus, rotation of the wheel 18 under the control of the stepper motor 186 moves the cover between the forward and rearward positions. Furthermore, reversing the rotation of the wheel between the positions shown in FIGS. 19 and 20 selectively moves the retaining member between the forward and rearward positions. An indention 193 in the arm 188 creates a slight amount of clearance between the projection 192 and the arm 188 when the wheel 182 is rotated through the arc-like segment to lift and lower the lift wire. Since one end of the arc-like segment of rotation which causes the lifting and lowering of the lift wire ends near the position shown in FIG. 19, this clearance prevents the retaining member from being moved or disturbed during the lifting and lowering of the lift wire.

Control over the lifting and lowering action of the lift wire 90 is also achieved by rotation of the wheel 182, as is shown in FIGS. 21 and 22. When the wheel 182 is rotated to position the first cylindrical projection 180 in the position illustrated in FIG. 21 (which is the same position shown in FIG. 19 to move the retaining member 70 to the forward position), the pivot arm 178 is allowed to pivot to its rearward most clockwise position as shown in FIG. 21. Rotating the wheel 182 clockwise as shown in FIG. 22 positions the projection 180 forwardly, thereby pivoting the pivot arm 178 to its forwardmost counterclockwise position. Because the lever arm 178 and the lift wire 90 are rigidly connected to the pivot shaft 170, the lift wire 90 alternates between the lifted and lowered positions shown respectively in FIGS. 22 and 21. Thus, rotating the wheel 182 through alternating arc-like paths between the positions shown in FIGS. 21 and 22 achieves a repeated lifting and lowering of the lift wire 90. Of course, the rate at which the wheel is rotated and the rate of movement through particular segments of the arc through which the wheel 182 rotates allows precise control over the linear movement of the plunger. The degree of rotation and the extent and rate of rotation is readily obtained by the stepper motor 186 under the precise control of the microprocessor computer.

As can be seen in FIGS. 21 and 22, the arc-like alternating rotational movement of the wheel 182 to lift and lower the lift wire rotates the projection 192 out of contact with the arm 188, positioning the retaining member 70 in the forward position during reciprocation of the lift wire and plunger assembly. In addition and as can be seen in FIGS. 19 and 20, rotation of the projection 192 in the arc-like path to move the retaining member between the forward and rearward position is also coordinated with the position of the lift wire so that the lift wire is in the lower position when the retaining member is forward and the lift wire is lifted when the retaining member is in the rearward position. With the lift wire 90 in the lower position as the retaining member 70 moves forward, the lift wire 90 will more reliably slide beneath the flags 42 of the plunger assembly 40 (FIGS. 4A and 4B), thereby assuring that the lift wire 90 is in position to lift and lower the plunger assembly 40 by contact with the flags 42 (FIGS. 4A and 4B). Also note that the arc segment through which the projections 180 and 192 rotate during movement of the retaining member to the forward position is different than the arc segment through which the projections rotate to lift and lower the lift wire. The two arc segments of rotation have only the common starting position illustrated in FIGS. 19 and 21.

Rotation of the wheel 182 controls the functions of the plunger lifting subassembly 88 during actual use in the following manner. From the starting position shown in FIG. 20, the wheel 182 rotates to the position shown in FIG. 19 to initially move the retaining member 70 to the initial forward position. In the initial forward position the information on the cartridge is read to determine the type of analytical test to be performed. Thereafter, the retaining member 70 is partially withdrawn to a position approximately half way to the rearwardmost position to allow the dispensing subassembly to fill the test cells of the cartridge with the samples of fluid. In this partially withdrawn position, the projection 192 is approximately between the positions shown in FIGS. 19 and 20. After the test cells have been filled with the fluid samples, the wheel 182 is rotated clockwise as shown in FIG. 20 past the position shown in FIG. 20. After the projection 192 clears the lower end of the arm 188, the retaining member moves forward under the force of the spring 174 (FIG. 14). Continued clockwise rotation as shown in FIG. 20 moves the projection 180 along the pivot arm 178 at a position near its outer end as the pivot arm pivots to commense lifting the lift wire. This initial lifting of the lift wire raises the disk member 46 of the plunger assembly 40 out of the opening 54 in the partition 56, thus opening the passageway between the reagent chamber 62 and the reaction chamber 63 (FIGS. 2 and 4A). Because the projection 180 is near the end of the pivot arm 178, more initial mechanical force is developed on the lift wire to overcome the force which seats the disk member 46 in the opening 54. Continued rotation of the wheel, clockwise as shown in FIG. 20 and counter clockwise as shown in FIG. 22, continues to raise the plunger assembly until the position shown in FIG. 22 is reached at the uppermost position of the initial lifting stroke. Thereafter the wheel 182 is alternatively rotated between the positions shown in FIGS. 21 and 22 to repeatedly lift and lower the plunger assembly during the analytical test. Since the force to lift and lower the plunger assembly during the test is considerably less than that force required to initially unseat the plunger assembly, contact of the projection 180 with the pivot lever 178 at positions closer to the pivot shaft 170, as is shown in FIGS. 21 and 22, is acceptable.

As is shown in FIGS. 14 and 16, vanes 194 and 195 are attached to the wheel 182. The vanes 194 and 195 intersect a light beam provided by optical sensors 196 and 197, respectively, to obtain signals representative of at least one the end points of movement or rotation of the wheel 182 through each of the two arc segments. The other end points of the rotation of the wheel are either obtained from the signals derived from the sensors 196 or 197, or from counting the energizing pulses supplied under microprocessor control to energize the plunger lifting stepper motor 186.

Details regarding the reagent drive subassembly 92 are illustrated in FIGS. 15 to 18. A relatively large amount of force is required to drive the plugs 58 (FIG. 4) upward in each of the tube-like members 36 of each test cell 34, at the commencement of the test to collapse the reagent chamber 62 (FIGS. 4A and 4B). Accordingly, a relatively larger reagent drive stepper motor 200 is used to achieve the necessary amount of force. An output shaft 20 of the reagent drive stepper motor 200 is connected to a gear 204 positioned on the shaft 202. A toothed belt 206, connects the gear 204 and a much larger diameter gear 208. The gear 208 is connected to a shaft 210 which is rotatably connected to a bearing 211 located on an interior mounting bracket 212 connected to the side frame plates 172. A cylindrical projection 213 extends forward from the gear 208. The projection 213 extends into an elongated slot 214 formed in the rear side of a drive bar 216. The drive bar 216 is slidably mounted on a pair of vertical guide rods 218 which extend between the receiving block 64 and a lower bracket 220 that extends between the side frame plates 172. Bushings (not shown) in the drive bar 216 surround the guide rods 218.

A pair of coiled springs 222 are installed concentrically on the guide rods 218 between the drive bar 216 and the lower bracket 220 and bias the drive bar 216 to counteract the effect of gravity.

A plurality of plug driver shafts 94 are attached to the drive bar 216 at predetermined locations to extend upward into the lower ends of the receptacle 66 in the receiving block 64. The plug driver shafts 94 contact the plugs 58 located in the bottom of each test cell 34 when the cartridge is in position. Rotation of the gear 208 causes the projection 213 to contact the elongated slot 214 and move the drive bar 216 vertically to the same extent that the projection 213 moves vertically during rotation of the gear 208. Thus, the drive bar 216 is reciprocated vertically by rotation of the gear 208. The upward vertical movement of the drive bar 216 causes the driver shafts 94 to push the plugs 58 upward, thereby collapsing the reagent chamber 62 and forcing the reagent 60 into the reaction chamber 63, as is illustrated in FIG. 4B.

The rotational position of the gear 208 and the vertical position of the drive bar 216 and driver shafts 94 is sensed by use of a projection 224 extending from the rear of the gear 208 and an optical sensor 226. The projection 224 breaks a light beam in the sensor 226 to derive a signal used by the microprocessor computer to control the reagent drive stepper motor 200 to achieve the positions indicated.

By separately controlling the movement of the drive bar and the lifting mechanism, the plugs 58 can be moved to collapse the reagent chamber independently of the plunger lifting movement. This has particular advantages in that the more substantial mechanical mass of the reagent drive subassembly 92 need not be operated simultaneously with the lifting and lowering of the plunger assembly, as was the case in the assignee's prior U.S. Pat. No. 4,599,219. A smaller more controllable motor may be employed to achieve the plunger lifting functions while the larger motor used for the reagent drive subassembly need only be operated to collapse the reagent chamber and then be stopped.

Thus, stepper motors used in conjunction with the present invention, the independent control over collapsing the reagent chamber, the degree and rate and manner of lifting and lowering the plunger assembly and the positioning, and the dispensing of the predetermined amounts of samples into each of the test cells, allows a higher degree of automation, more precise control, less mechanical noise and vibration in the apparatus, which causes less disruption. As a consequence, smaller amounts of the sample may be used to allow more precise detection of the coagulation activity.

A presently preferred embodiment of the present invention and many of its improvements have been described with a degree of particularity. It should be understood that this description has been made by way of preferred example, and that the invention is defined by the scope of the following claims.

The invention claimed is:

1. In an apparatus for conducting an analytical test to detect coagulation related activity of a sample of fluid using a plunger sensing cartridge, the cartridges including at least one vertically extending tube-like test cell having a reagent initially confined in a reagent chamber, the reagent chamber defined in part by a movable plug member movably positioned at a lower end of the test cell, the test cell also including a reaction chamber located above the reagent chamber and extending to an open upper end of the test cell, the reaction chamber containing the sample of fluid, the reaction chamber connected in fluid communication with the reagent chamber by a passageway, the cartridge further including a plunger assembly located in the reaction chamber and retained for generally vertical reciprocative movement within the sample of fluid contained in the reaction chamber, said apparatus comprising plunger lifting means for contacting the plunger assembly and operatively lifting the plunger assembly within the sample of fluid in the reaction chamber and releasing the plunger assembly to allow a fluid resistance property of the sample to control the descent of the plunger assembly, said apparatus further comprising reagent drive means for moving the plug member upward to collapse the reagent chamber and force the reagent through the passageway into the reaction chamber prior to commencement of the test; and an improvement to said apparatus in combination therewith comprising:

dispensing means for automatically dispensing a predetermined quantity of a sample of the fluid to be tested into each reaction chamber through the open end of each test cell prior to the commencement of the test, the dispensing means dispensing the sample prior to the plunger lifting means contacting the plunger assembly for the lifting and releasing of the plunger assembly.

2. An improved apparatus as defined in claim 1 wherein:

each of the dispensing means, the plunger lifting means and the reagent drive means include a separate motor means for operating each; and the motor means of each of the dispensing means, the plunger lifting means and the reagent drive means is each separately controllable independently of the other.

3. An improved apparatus as defined in claim 1 wherein:

the motor means of each of the dispensing means, the plunger lifting means and the reagent drive means is a stepper motor.

4. An improved apparatus as defined in claim 1 wherein the dispensing means further comprises:
a needle-like conduit through which the sample of fluid is dispensed into the reaction chamber; and wherein:
the needle-like conduit is inserted into the open upper end of the test cell and beside a portion of the plunger assembly prior to dispensing the sample into the reaction chamber.

5. An improved apparatus as defined in claim 4 wherein:
the dispensing means inserts the needle-like conduit and withdraws the needle-like conduit in vertical movements; and
the plunger lifting means contacts the plunger assembly after the needle-like conduit is withdrawn from the test cell.

6. An improved apparatus as defined in claim 4 wherein the dispensing means further comprises:
means for accepting and holding a conventional medical syringe having a tubular body with an open first end into which a syringe plunger is movably fit and a second end from which fluid contained in the body is expelled upon movement of the syringe plunger toward the second end, the needle-like conduit connected to the second end of the syringe; and
syringe plunger drive means for driving the syringe plunger into the syringe body to expel a predetermined amount of the sample of fluid from the syringe body and through the needle-like conduit.

7. An improved apparatus as defined in claim 6 further comprising:
means for retaining and selectively detaching the syringe to the dispensing means.

8. In an apparatus for conducting analytical tests to detect coagulation related activity of samples of fluids using a plunger sensing cartridge, the cartridge including a plurality of vertically extending tube-like test cells, each test cell having a reagent initially confined in a reagent chamber, the reagent chamber defined in part by a moveable plug member movably positioned at a lower end of the test cell, the test cell also including a reaction chamber located above the reagent chamber and extending to an open upper end of the test cell, the reaction chamber containing a sample of fluid, the reaction chamber connected in fluid communication with the reagent chamber by a passageway, the cartridge further including a plunger assembly located in the reaction chamber of each test cell and retained for generally vertical reciprocative movement within the sample of fluid contained in the reaction chamber, said apparatus comprising reagent drive means and plunger lifting means, the reagent drive means moving the plug member of each test cell upward to collapse the reagent chamber and force the reagent through the passageway into the reaction chamber in each test cell, the plunger lifting means operatively lifting the plunger assembly within the sample of fluid in the reaction chamber of each test cell and releasing the plunger assembly to allow a fluid resistance property of the sample in the reagent chamber to control the descent of each plunger assembly, the descent of the plunger assembly against the resistance of the sample thereby indicating the coagulation related activity of the fluid; and an improvement in combination therewith comprising:
dispensing means for automatically dispensing a predetermined quantity of a sample of the fluid to be tested into each reaction chamber of each test cell of the cartridge, the dispensing means further comprising:
movement means operatively positioned with respect to the cartridge in the apparatus for lateral movement with respect to the vertical extension of the test cells of the cartridge;
syringe retaining means connected to the movement means and operative for accepting and holding a conventional medical syringe having a tubular body with an open first end into which a syringe plunger is movably fit and a second end from which fluid contained in the body is expelled upon movement of the syringe plunger toward the second end; and
syringe plunger drive means connected to the movement means and operative for driving the syringe plunger into the syringe body to expel a predetermined amount of the sample of fluid from the second end of the syringe body;
the movement means operatively moving the syringe to a predetermined position relative to each reaction chamber of each of the test cells of the cartridge to deliver the expelled sample of fluid into each reaction chamber.

9. An apparatus as defined in claim 8 wherein:
the syringe further includes a needle connected to the second end of the body and through which the sample of fluid is expelled; and
the movement means positions the syringe over each test cell of the cartridge in the apparatus and moves the syringe toward each test cell to insert the needle within each reaction chamber prior to the syringe plunger drive means expelling the sample.

10. An apparatus as defined in claim 9 wherein:
the movement means moves the syringe and the syringe plunger drive means expels the sample cooperatively to fill each reaction chamber of the cartridge in sequence.

11. An apparatus as defined in claim 9 wherein:
the movement means moves the syringe laterally over each test cell and moves the syringe vertically to insert the needle within each reaction chamber;
the syringe plunger drive means further includes a syringe plunger drive motor means for controlling the amount of movement of the syringe plunger to expel the sample; and the improved dispensing means further comprises:
lateral guide means connected to and operative for guiding the movement means laterally;
vertical guide means connected to and operative for moving the syringe retaining means and the syringe plunger drive means vertically;
lateral movement motor means connected to the movement means and operative for moving the movement means laterally along the lateral guide means; and
vertical movement motor means connected to the movement means and operative for moving the syringe retaining means and the syringe plunger drive means vertically;
the lateral movement motor means and the vertical movement motor means and the syringe plunger drive motor are each controllable independently of the other.

12. An apparatus as defined in claim 9 further comprising:
a main block member;

a dispensing subassembly frame attached to said apparatus, the dispensing subassembly frame including a left vertical side member and a right vertical side member spaced from one another on opposite sides of the dispensing subassembly frame;

at least one horizontal guide rod attached to and extending between the vertical side members along an axis of lateral movement, the main block member slidably mounted to the horizontal guide rod to permit lateral movement of the main block member between the vertical side members;

a threaded rod extending between vertical side members in a parallel relationship to the horizontal guide rod;

a rotatable member rotatably connected in threaded engagement with the threaded rod and connected to main block member to move the main block member laterally along the horizontal guide rod when rotated; and a lateral movement motor operatively connected to the main block member and to rotate the rotatable member to move the main block member along the horizontal guide rod.

13. An apparatus as defined in claim 12 wherein:
the rotatable member comprises a hollow armature of the lateral movement motor, the hollow armature having an internal thread in engagement with the threaded rod.

14. An apparatus as defined in claim 12 further comprising:
at least one vertical guide rod operatively connected to the main block member and extending along an axis of vertical movement;
a support plate slidably mounted on the vertical guide rod;
a track member positioned in a vertical orientation and operatively connected to the support plate;
a vertical movement motor connected to the main block member and having an output rotational member engaging the track member to vertically move the track member and the connected support plate upon rotation of the output rotational member by the vertical movement motor.

15. An apparatus as defined in claim 14 wherein:
the track member has a linear toothed surface oriented parallel to the vertical guide rod; and
the output rotational member is a gear having teeth which engage the teeth of the track member.

16. An apparatus as defined in claim 14 further comprising:
a notch in the vertical track member; and
detent means operatively connected to the main block member and operative to engage the notch and restrain the vertical track member and the attached support plate against vertical movement.

17. An apparatus as defined in claim 14 wherein the syringe plunger includes a rib extending therealong, and said syringe plunger drive means further comprises:
a drive wheel positioned in a fixed position at the support plate above the syringe retaining means to rotatably engage the rib of the syringe plunger and move the syringe plunger vertically;
engagement means operatively attached to the support plate at a position opposite the drive wheel, the rib of the syringe plunger extending between the engagement means and the drive wheel, the engagement means operative for forcing the rib of the syringe plunger into frictional engagement with the drive wheel to transfer rotational movement of the drive wheel into linear movement of the syringe plunger; and
a syringe plunger drive motor operatively connected to the support plate and operatively connected to rotate the drive wheel.

18. An apparatus as defined in claim 17 wherein the syringe plunger drive means further comprises:
a drive shaft connected at one end to the drive wheel and rotatably supported relative to the support plate;
a worm gear attached to the other axial end of the drive shaft; and
a worm screw attached to the output shaft of the syringe plunger drive motor and meshing with and driving the worm gear.

19. An apparatus as defined in claim 14 wherein:
the syringe retaining means is connected to the support plate, and the syringe retaining means further comprises:
a bracket attached to the support plate and having a keyhole shaped opening of a configuration adapted to receive a portion of the needle attached to the syringe body;
a retaining block attached to the support plate above the bracket and having an elongated channel oriented vertically and aligned directly above the keyhole shaped opening in the bracket, the channel receiving the syringe body therein when the portion of the needle is inserted in the keyhole shaped opening of the bracket;
latching means for latching the syringe body into the channel of the retaining block; and
switch means connected relative to the retaining block to be actuated by latched reception of the syringe body in the channel of the retaining block.

20. In an apparatus for conducting analytical tests to detect coagulation related activity of samples of fluids using a lunger sensing cartridge, the cartridge including a plurality of vertically extending tube-like test cells, each test cell having a reagent initially confined in a reagent chamber, the reagent chamber defined in part by a movable plug member movably positioned at a lower end of the test cell, the test cell also including a reaction chamber located above the reagent chamber and extending to an open upper end of the test cell, the reaction chamber containing a sample of fluid, the reaction chamber connected in fluid communication with the reagent chamber by a passageway, the cartridge further including a plunger assembly located in the reaction chamber of each test cell and retained for generally vertical reciprocative movement within the sample of fluid contained in the reaction chamber, each plunger assembly including a plunger shaft extending through the reaction chamber and terminating with at least one flag located exteriorly of and spaced from the open end of the test cell, said apparatus comprising reagent drive means and plunger lifting means, the reagent drive means moving the plug member of each test cell upward to collapse the reagent chamber and force the reagent through the passageway into the reaction chamber in each test cell, the plunger lifting means lifting the plunger assembly within the sample of fluid in the reaction chamber of each test cell and releasing the plunger assembly to allow a fluid resistance property of the sample to control the descent of the plunger assembly, the descent of the plunger assembly against the resistance of the sample thereby indicating the coagulation related activity of the fluid; and an improvement to said plunger lifting means comprising:

a frame member;

a retaining member retained to the frame member and moveable to a front and a rear position in which to hold the cartridge in place for testing and to allow the insertion and removal of cartridge, respectively;

an arm operative attached to the retaining maimer at a rearward position thereof and expending generally downward from the retaining member;

a pivot shaft pivotably mounted to and carried by the retaining member;

at least one plunger lift wire connected to the pivot shaft carried by the retaining member, the lift wire including a segment extending parallel to the axis of the pivot shaft at a position radially spaced from the axis of the pivot shaft at a forward location of the retaining member;

a lever connected to the pivot shaft and extending radially outward in a generally downward and rearward direction from the pivot shaft;

a plunger lift motor attached to the frame member, the plunger lift motor having an output shaft;

a wheel connected to and rotational about an axis of the output shaft for the plunger lift motor, the wheel rotational axis located in a generally downward and rearward location relative to the retaining member;

a first projection extending from the wheel at an eccentric position relative to the wheel rotational axis and located to contact the arm upon rotation of the wheel through a first predetermined arcuate segment, the contact of the first projection with the arm during rotation of the wheel through the first predetermined segment of rotation moving the arm and the connected retaining member between the rearward and forward positions;

a second projection extending from the wheel at an eccentric position relative to the wheel rotational axis and located to contact the lever upon rotation of the wheel through a second predetermined arcuate segments, the contact of the second projection with the lever during rotation of the wheel through the second predetermined segment of rotation to pivot the pivot shaft and the attached lift wire and move the horizontal segment of the lift wire with alerting and lowering movement.

21. An apparatus as defined in claim 20 wherein:

the orientation of the first projection and the second projection on the wheel and the contact positions of the arm and the lever with the first and second projections allowing the rotation of the wheel through the first and second predetermined arcuate segments to obtain the movement of the retaining member between the forward and rearward positions to occur both conjunctively with and independently of the raising and lowering of the lift wire depending upon the direction and extent of rotation of the wheel.

22. An apparatus as defined in claim 21 wherein:

the orientation of the first projection and the second projection on the wheel and the contact positions of the arm and the lever with the first and second projections allowing the rotation of the wheel in the first predetermined arcuate segment to obtain the forward movement of the retaining member while simultaneous lowering the horizontal segment of the lift wire to a position below the flag members of the plunger assembly.

23. An apparatus as defined in claim 21 wherein:

the first and second predetermined arcuate segments of rotation are different from one another.

24. An apparatus as defined in claim 16 wherein:

at least one vane extending from the wheel and having a mechanical configuration defining at least a portion of at least one of the two predetermined arcuate segments of rotation; and sensor means operatively connected to the frame member at a position to sense the position of the vane during rotation of the wheel in at least one of the two predetermined arcuate segments of rotation.

25. An apparatus as defined in claim 20 wherein:

the orientation of the first projection and the second projection on the wheel and the contact positions of the arm and the lever with the first and second projections allowing the rotation of the wheel in the first predetermined arcuate segment to obtain the forward movement of the retaining member while simultaneous lowering the horizontal segment of the lift wire to a position below the flag members of the lunger assembly.

26. In an apparatus for conducting analytical tests to detect coagulation related activity of samples of fluids using a plunger sensing cartridge, the cartridge including a plurality of vertically extending tube like test cells, each test cell having a reagent initially confined in a reagent chamber, the reagent chamber defined in part by a moveable plug member movably positioned at a lower end of the test cell, the test cell also including a reaction chamber located above the reagent chamber and extending to an open upper end of the test cell, the reaction chamber containing a sample of fluid, the reaction chamber connected in fluid communication with the reagent chamber by a passageway, the cartridge further including a plunger assembly located in the reaction chamber of each test cell and retained for generally vertical reciprocative movement with the sample of fluid contained in the reaction chamber, said apparatus comprising a receiving block having a receptacle for receiving each one of the plurality of tube like test cells of the cartridge, the bottom of each receptacle being open, reagent drive means including a drive rod extending to project into the open bottom of each receptacle to contact and move the plug member of each test cell to collapse the reagent chamber and force the reagent through the passageway into the reaction chamber in each test cell, plunger lifting means for lifting the plunger assembly within the sample of fluid in the reaction chamber of each test cell and releasing the plunger assembly to allow a fluid resistance property of the sample to control the descent of each plunger assembly, the descent of the plunger assembly against the resistance of the sample thereby indicating the coagulation related activity of the fluid; and an improvement to said reagent drive means comprising:

a frame member;

a reagent drive motor connected to the frame member and having an output shaft to be rotated by the reagent drive motor;

a first drive wheel attached to the output shaft of the reagent drive motor;

a second drive wheel rotatably mounted at a fixed position relative to the frame member;

a belt rotatably connecting the first and second drive wheels;

a projection extending from the second drive wheel at an eccentric position relative to the rotational axis of the second drive wheel;

at least one vertical guide rod attached to the frame member and the receiving block;

a drive bar slidably mounted on the vertical guide rod to travel in a direction parallel to the extent of the vertical guide rod, each drive rod connecting to the drive bar; and an elongated sot formed in the drive bar and operatively positioned to receive therein the projection extending from the second drive wheel;

the engagement of the projection with the slot translating rotation movement of the second drive wheel into linear movement of the drive bar to extend each drive rod into the open ends of the receptacles upon movement of the drive bar toward the receiving block to push the plug members and collapse the reagent chamber.

27. An apparatus as defined in claim 26 further including:

at least one locating member extending from the second drive wheel; and sensor means operatively connected to the frame member at a position to sense the position of the locating member during rotation of the second drive wheel to determine the position of the drive bar and connected drive rods.

* * * * *